United States Patent [19]

Steward, Jr.

[11] Plant 4,367

[45] Jan. 16, 1979

[54] AMERICAN HOLLY—STEWARD'S SILVER CROWN VARIETY

[76] Inventor: T. Linwood Steward, Jr., R.F.D. Lambs Rd., Pitman, N.J. 08071

[21] Appl. No.: 764,529

[22] Filed: Jan. 31, 1977

[51] Int. Cl.[2] ..... A01H 5/00

[52] U.S. Cl. ..... Plt./65

[58] Field of Search ..... Plt./65

[56] References Cited

U.S. PATENT DOCUMENTS

P.P. 3,517 3/1974 Meserve ..... Plt./65

*Primary Examiner*—Robert E. Bagwill

*Attorney, Agent, or Firm*—Burns, Doane, Swecker & Mathis

[57] ABSTRACT

A new and distinct variety of American Holly plant, *Ilex opaca,* is provided having variegated leaves (as described). The new variety occurred as a mutation on a portion of a seven year old female American Holly plant growing at Pitman, N.J. The upper side of the newly formed leaves exhibits an off-white border having a pinkish cast and two-toned mottled dark and light green center disc portion. The pinkish cast of the leaf border tends to disappear as the leaves mature. The new variety abundantly forms red berries.

2 Drawing Figures

SUMMARY OF THE INVENTION

The new and distinct variety of American Holly plant, *Ilex opaca,* was discovered in 1956 as a mutation that developed on a seven year old chance seedling of the American Holly variety growing in a cultivated area at my nursery in Pitman, N.J. The mutation occurred as a single leaf which possessed the variegated appearance described hereafter and attracted my attention as being distinctive. The other leaves of the American Holly plant on which the mutation occurred possessed the usual green appearance characteristic of that variety.

In accordance with terminology heretofore utilized with variegated English Holly varieties the new and distinct variety of American Holly can be termed a "silver" variegated variety. The upper side of the newly formed leaves exhibits an off-white border having a pinkish cast and two-toned mottled dark and light green center disc portion. The pinkish cast of the leaf border tends to disappear as the leaves mature. The new variety abundantly yields red berries.

This new variety of American Holly has been named STEWARD'S SILVER CROWN VARIETY.

Asexual reproduction of my new and distinct variety by hardwood cuttings at Pitman, N.J. shows that its unique combination of characteristics come true to form and are established and transmitted through succeeding propagations. The new variety can be easily propagated.

BRIEF DESCRIPTION OF THE DRAWINGS

The photographs depict the new variety in color as nearly true as it is reasonably possible to make the same in color illustrations of this character.

DETAILED DESCRIPTION OF THE DISCLOSURE

The following description was made of plants of the new and distinct variety growing at Pitman, N.J. Color designations are specified in accordance with their usual dictionary significance.

Growth Habit: Attractive, tall, upright, evergreen, outdoor shrub or tree; for garden decoration and general landscape use.

Genus and Species: *Ilex opaca.*

Parentage: The new variety occurred as a mutation on a seven-year-old chance seedling of the American Holly variety.

Hardiness: Excellent.

Propagation: It does hold its distinguishing characteristics through succeeding propagations by hardwood cuttings.

Foliage: The leaves are simple and alternate. The leaves are similar to those of the common American Holly except for the distinctive variegated leaf appearance described hereafter. The maximum leaf dimensions are approximately 10 cm. (length) × 4.4 cm. (width). Mature leaves commonly are about 3.6 to 4.4 cm. in width and about 5.3 to 8.2 cm. in length. The leaves are serrate with about 5 to 10 sets of spiny teeth, apex acute, texture stiff firm. The leaf spines are approximately 0.6 cm. in length. See FIGS. 1 and 2.

*Color.*—Upper Side: Newly formed leaves exhibit an off-white (i.e. creamy white) border having a pinkish cast and a two-toned mottled dark and light green center disc portion. The pinkish cast of the leaf border tends to disappear as the leaves mature, but may be retained by some mature leaves to a slight degree. Otherwise the variegated appearance is retained even in mature leaves. Under Side: Pale green.

Flowers: Pistillate flowers are borne in clusters on the previous season's growth. Flowers are carried on short stiff peduncles of greenish color tending to become reddish at the base. Bud form is ovoid, smooth with generally cream color. Bloom when fully open is 5 to 8 mm. in diameter with four petals arranged regularly. Petals are white. Male blossoms are absent.

Reproductive organs: All the flowers are pistillate and have one pistil centered in the flower. The pistil color is yellowish at the apex with a greenish base.

Fruit: Round, glossy, intense red, size — approximately 8 to 9 mm. in diameter; formed in large quantities on new wood. Immature fruit is longitudinally striped, alternately light green and cream. Ripening takes place from late September to the middle of October at Pitman, N.J. Fruit retention is excellent being retained on the plant frequently into the next blooming season.

Bark Color: Light gray to mouse gray.

Drought Resistance: Normal.

Disease Resistance: Normal.

Figure 1:
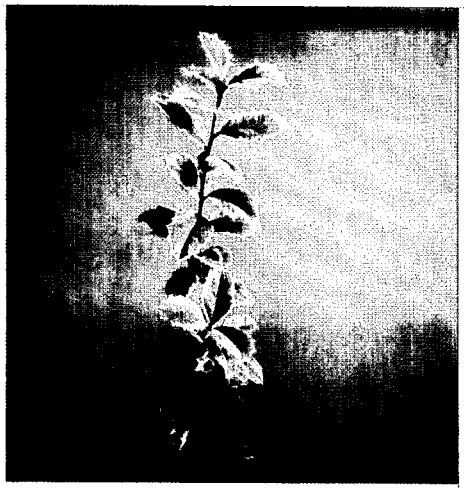
FIGS. 1 and 2 show typical specimens of a one-year-old plant of the new variety growing at Pitman, New Jersey wherein the variegated appearance of the upper surface of the leaves is apparent. Since the photographs of FIGS. 1 and 2 were made during the fall, and the leaves have had an opportunity to mature, the pinkish cast found in the off-white border of newly formed leaves of this variety no longer is observable.
Figure 2:
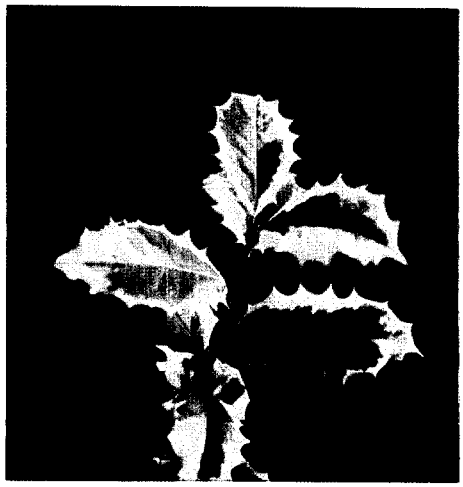

The present Steward's Silver Crown variety is distinct from my Steward's Cream Crown variety (American Holly Society Registration No. 1-63). The Steward's Cream Crown variety has been observed by me for a number of years and never has been sold commercially and never has left my control. Each variety has leaves which on the upper surface possess marginal variegation; however, their leaf appearances are markedly different. More specifically, the newly formed leaves of the Steward's Silver Crown variety on the upper surface are pinkish in color, while the newly formed leaves of the Steward's Cream Crown variety on the upper surface are light green in color. Also, the border of the mature leaves of the Steward's Silver Crown variety is an off-white color as illustrated in FIGS. 1 and 2, while the border of the mature leaves of the Steward's Cream Crown variety is more yellow in color. Both varieties are female and bear red berries.

The upper surfaces of the leaves of Steward's Silver Crown Variety are more glossy than those of Steward's Cream Crown variety. Also, the leaves of the present variety are thicker than those of Steward's Cream Crown variety.

The following color description of Steward's Silver Crown variety was made with the aid of the R.H.S. Colour Chart of the Royal Horticultural Society, London. The upper surfaces of mature leaves generally exhibit four distinct variations in color ununiformly blotched in overlying layers. The darkest of such color variations is near Green Group 137A, the most intense intermediate coloration is near Yellow-Green Group 148B, the lightermost intermediate coloration is near Yellow-Green Group 145C, and the lightest color variation which occurs predominantly uniformly around the margins of the leaves is near Yellow Group 4B. The undersides of the leaves exhibit a substantially green coloration between Yellow-Green Group 147C and 148B with a marginal variegation near Yellow Group 4B. Recently formed leaves exhibit a pinkish blush ranging in coloration between Red Group 54D and 55D which is exhibited on both the top and underside of the leaves. The stem coloration of old growth is near Greyed-Green Group 197B, and the stem coloration of new growth is near Green Group 138C.

I claim:

1. A new and distinct variety of American Holly (*Ilex opaca*) resulting as a mutation on a portion of chance seedling growing in a cultivated area exhibiting (a) variegated newly formed leaves having an upper side which possesses an off-white border with a pinkish cast and a two-toned mottled dark and light green center portion, and (b) the propensity to abundantly form red berries, substantially as shown and described.

* * * * *